(12) United States Patent
Tsay

(10) Patent No.: US 7,222,760 B1
(45) Date of Patent: May 29, 2007

(54) DRIVING MECHANISM FOR FRAGRANCE DISPENSER

(76) Inventor: Chyuan-Feng Tsay, PO Box 82-144, Taipei (TW)

( * ) Notice: Subject to any disclaimer, the term of this patent is extended or adjusted under 35 U.S.C. 154(b) by 0 days.

(21) Appl. No.: 10/067,355

(22) Filed: Feb. 7, 2002

(51) Int. Cl.
*G04C 23/00* (2006.01)
(52) U.S. Cl. .................... 222/642; 222/504; 239/70
(58) Field of Classification Search ........... 222/642, 222/649, 183, 162, 504; 239/70
See application file for complete search history.

(56) References Cited

U.S. PATENT DOCUMENTS 4,235,373 A * 11/1980 Clark ........................ 239/70
5,249,718 A * 10/1993 Muderlak ................. 222/642
5,449,117 A * 9/1995 Muderlak et al. ............ 239/70

FOREIGN PATENT DOCUMENTS

EP    511006 A1 * 10/1992 ............ 222/642

* cited by examiner

*Primary Examiner*—Philippe Derakshani
(74) *Attorney, Agent, or Firm*—Leong C. Lei

(57) ABSTRACT

A driving mechanism for fragrance dispenser is disclosed. The driving mechanism comprises a press mechanism and a control circuit characterized in that the press mechanism is provided with a base seat having a protruded circular recess at the lower section thereof for the mounting of a fragrance bottle, the surface of the base seat is mounted with engageable main and driven gears, and the bottom of the base seat is provided with a motor such that the axle of the motor and the main gear are engaged with each other, and the driven gear is engaged with a press rod having a plurality of teeth such that the driving by the control circuit will drive the gear to rotate and the press rod is driven to move up and down, thereby the dispensing head of the fragrance bottle is pressed and the fragrance is dispensed at a specific timing.

1 Claim, 7 Drawing Sheets

DRIVING MECHANISM FOR FRAGRANCE DISPENSER

BACKGROUND OF THE INVENTION (a) Technical Field of the Invention

The present invention relates to a fragrance dispenser, and in particular, to a fragrance dispenser which can be operated smoothly with low noise to dispense fragrance at a specific time.

(b) Description of the Prior Art

Conventional fragrance dispenser is provided with a driving mechanism having gears to directly transmit the driving. After the motor of the dispenser is locked with a locking plate, the locking plate is then mounted onto a base seat. This conventional structure may produce poor movement as a result of poor engagement of gears. Besides, noise is produced and the electronic circuit for such conventional fragrance dispenser can only provide timing setting and the remaining amount of fragrance cannot be contrary. Accordingly, it is an object of the present invention to provide a driving mechanism for fragrance dispenser which mitigates the above drawbacks.

SUMMARY OF THE INVENTION

Accordingly, it is an object of the present invention to provide a driving mechanism for fragrance dispenser, wherein the driving movement of the dispenser is smoother and the noise production is low, and the fragrance dispensing time and amount can be easily controlled. Another object of the present invention is to provide an improved structure of a driving mechanism for a fragrance dispenser, wherein the driving mechanism includes a base seat, a motor positioned at the bottom section of the base seat and the axle of the motor is in engagement with the main driven gear which is geared to a press rod with row of teeth, thereby the transmission of the motor causes the press rod to press against the press button of the fragrance bottle, and the noise can be reduced and the transmission of the mechanism is smooth.

Yet another object of the present invention is to provide a driving mechanism for a fragrance dispenser, wherein the base seat is provided with a protruded fragrance bottle fixing slot, facilitating the fixing of the fragrance bottle.

A further object of the present invention is to provide a driving mechanism for a fragrance dispenser, wherein the mechanism includes a microprocessor, CPU and memories forming into a control circuit, thereby, the number of working day, the total number of dispensing can be set and controlled.

The foregoing object and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENT

Figure 1:
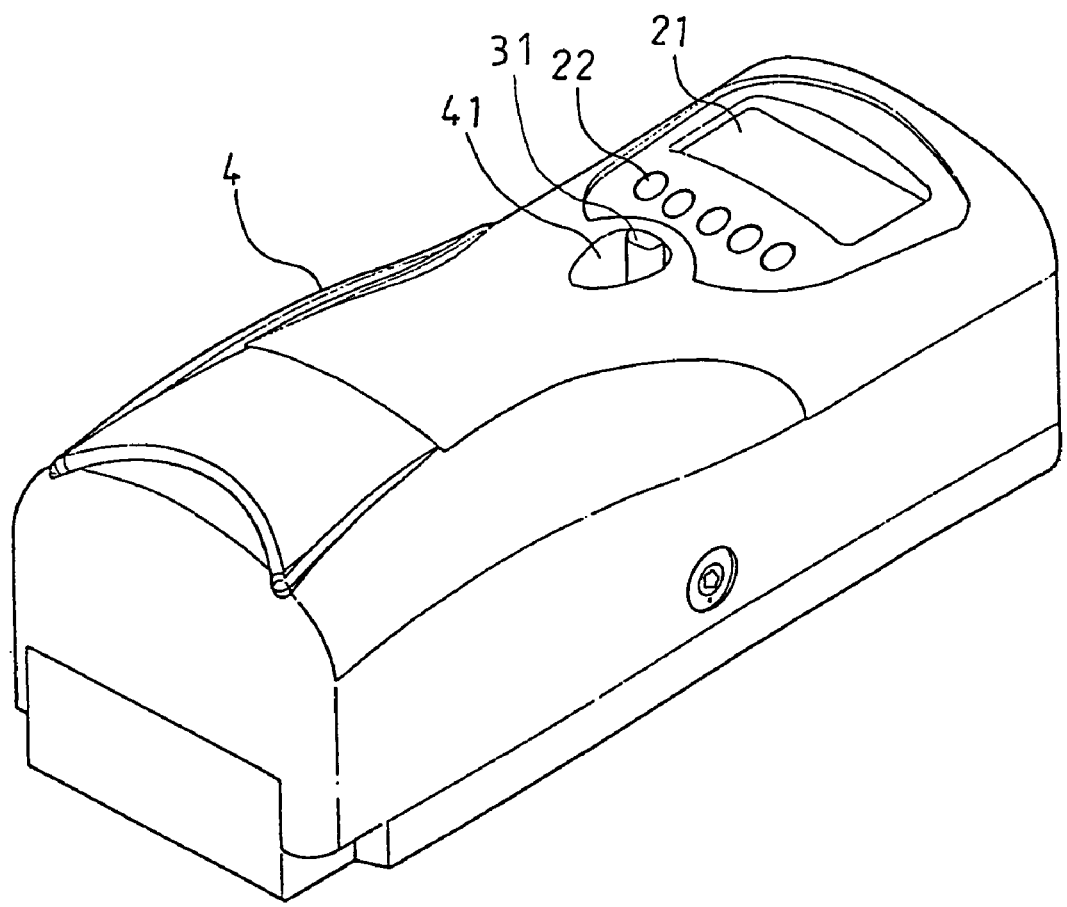
FIG. 1 is an exploded perspective view of the driving mechanism in accordance with the present invention.
Figure 2:
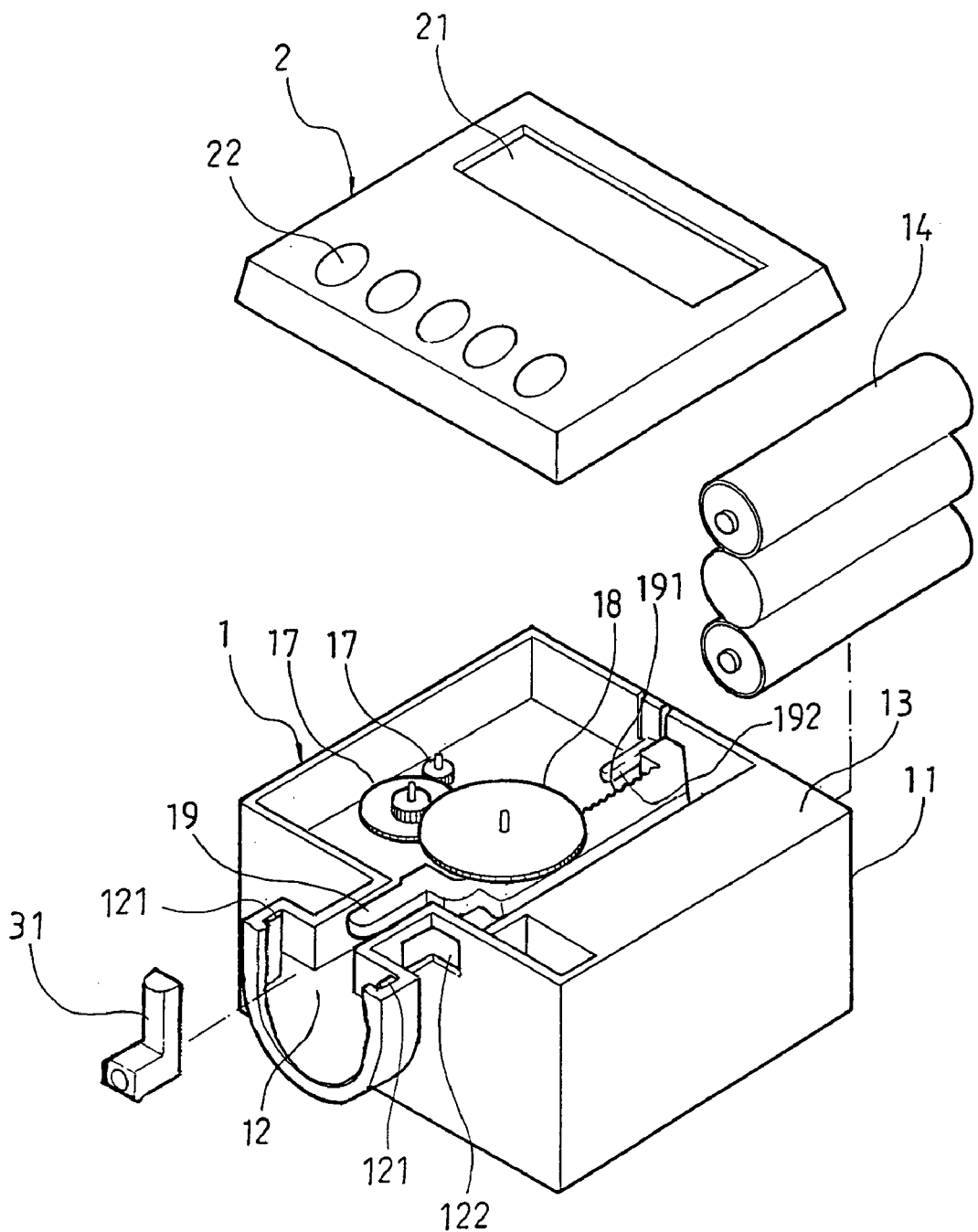
FIG. 2 is a perspective view showing the combination of the control circuit and the press mechanism in accordance with the present invention.
Figure 3:
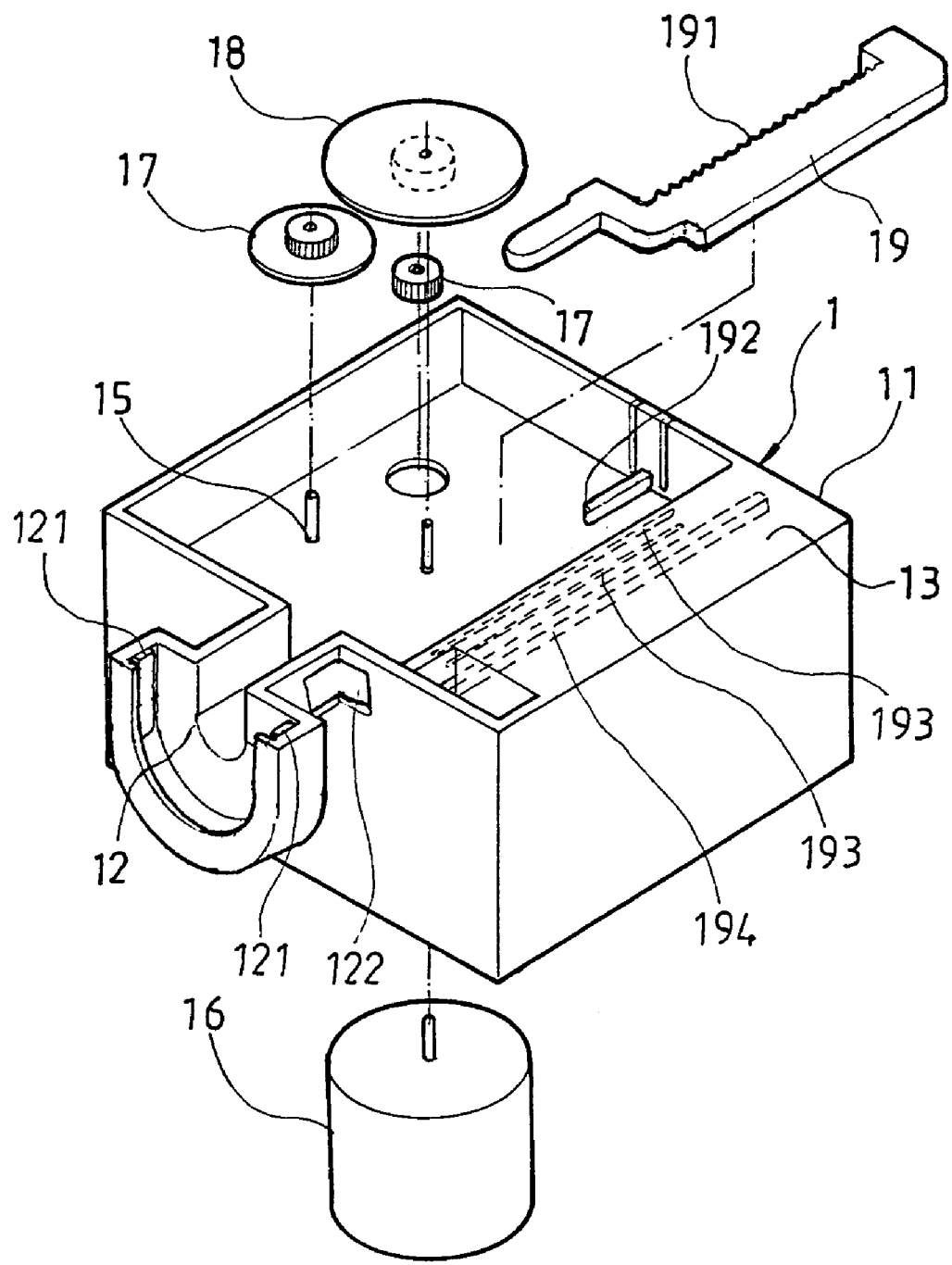
FIG. 3 is a perspective exploded view of the press mechanism in accordance with the present invention.
Figure 4:
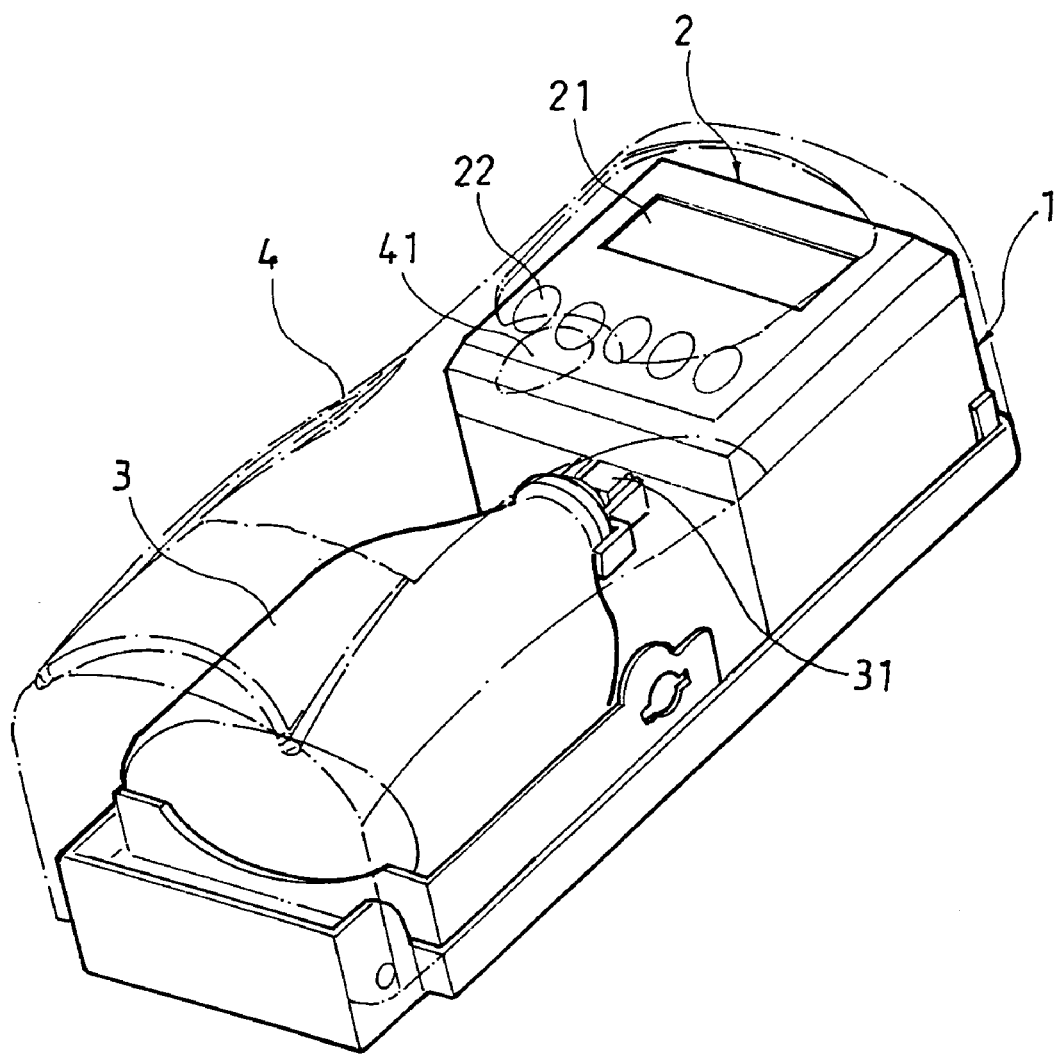
FIG. 4 is a perspective view of the dispensing mechanism in accordance with the present invention.

The following descriptions are of exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Referring to FIGS. 1, 2, 3 and 4, there is shown a driving mechanism for a fragrance dispenser which comprises a press mechanism 1, and a control circuit 2, wherein the press mechanism 1 includes a base seat 11 having a protruded circular recess 12 at the lower section of the base seat 11. The two lateral sides of the recess 12 are provided with fixing ribs 121, and at the connection between the recess 12 and the base seat 11 an opening 122 is formed. The opening 122 is used for the fixing of a fragrance bottle 3. The lateral side of the base seat 11 is provided with a battery compartment 13 for the holding of batteries 14. The surface of the base seat 11 is provided with a fixing hole 15 at an appropriate position for the mounting of a motor 16, from the bottom section of the base seat 11, so that the axle of the motor is protruded from the fixing hole 15, and at the axle and the fixing hole 15, a main and driven gear 17, 18 are respectively mounted thereto. The driven gear 18 is connected to a press rod 19 and one side of the press rod 19 is provided with a plurality of teeth 191. The press rod 19 urges the blocking ribs 192, 194 at the two lateral sides such that when the motor 16 rotates, the press rod 19 is driven to press downward. Thus, the spray head 31 of the fragrance bottle is pressed, and the fragrance is dispensed. In order to cause the press rod 19 to move smoothly, the surface of the base seat 11 below the press rod 19 is provided with a protruded rib 193, so that the movement of the press rod 19 is smooth.

In accordance with the present invention, the control circuit 2 includes a LCD 21 and a plurality of press buttons 22. By pressing the buttons 22, the number of working days and the total number of dispensing of the fragrance bottle 3 can be set. By means of the electronic circuit, the set time to active the driving motor 16 to dispense fragrance can be obtained.

The press mechanism 1 and the control circuit 2 are mounted within a specific designed dispenser body 4 and the fragrance bottle is mounted onto the recess 12 of the base seat 11. By means of the fixing rib 121, the bottle is mounted and the dispensing head is located at a positioning rod 31 facing the press rod 19 of the press mechanism 1. When the control circuit 2 drives the press mechanism 1, the press rod 19 is depressed downward and the dispensing head 31 is pressed and the fragrance from the fragrance bottle 3 is dispensed via the nozzle 41 of the dispenser body 4 and the environment is provided with a fragrance odor.

In order to smoothly depress the press rod 19, the notch 122 allows the front end of the press rod 19 to be protruded so that the press rod 19 is avoided from blockage.

Figure 5:
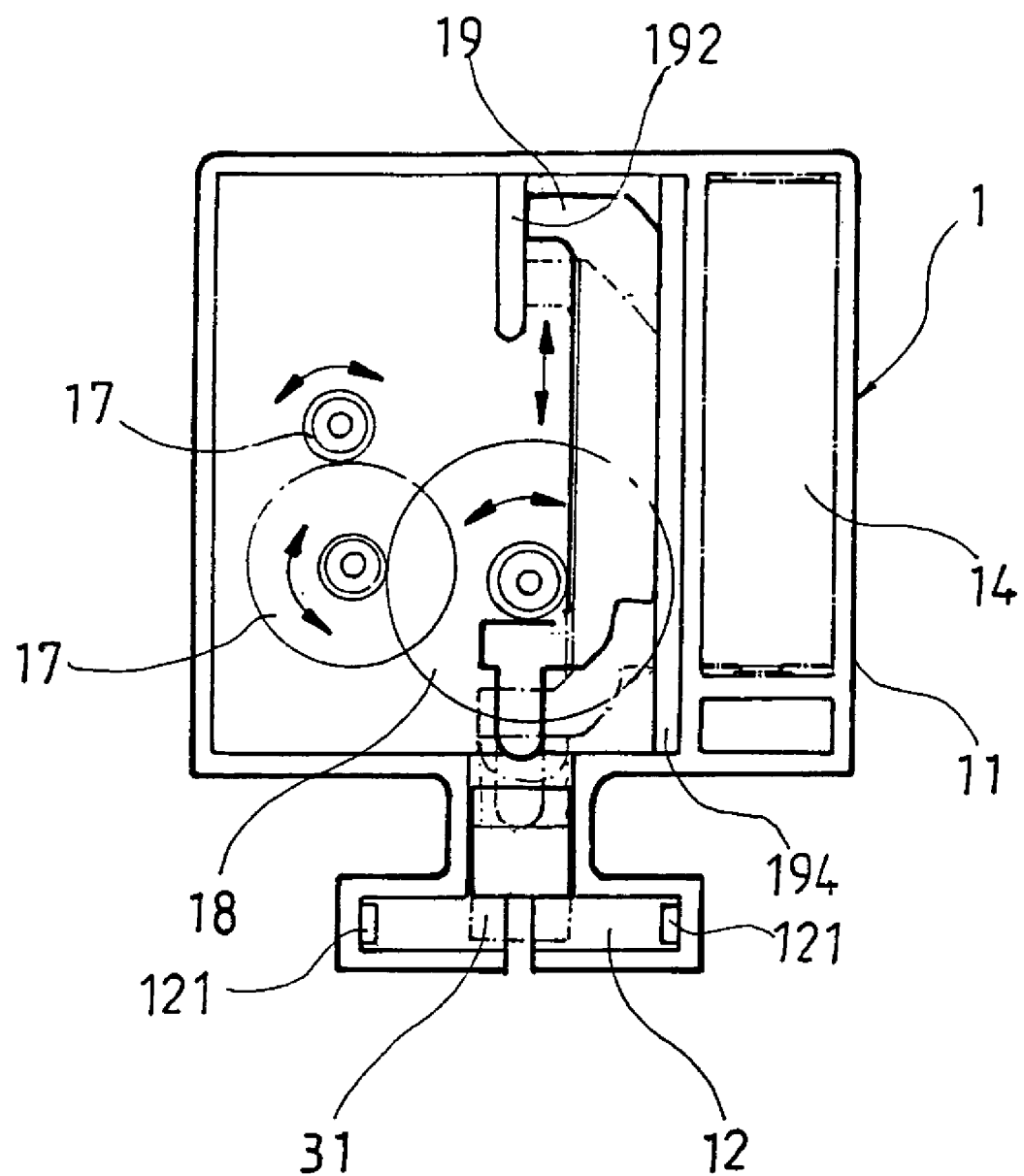
FIGS. 5 and 6 are schematic views showing the action of the present invention.
Figure 6:
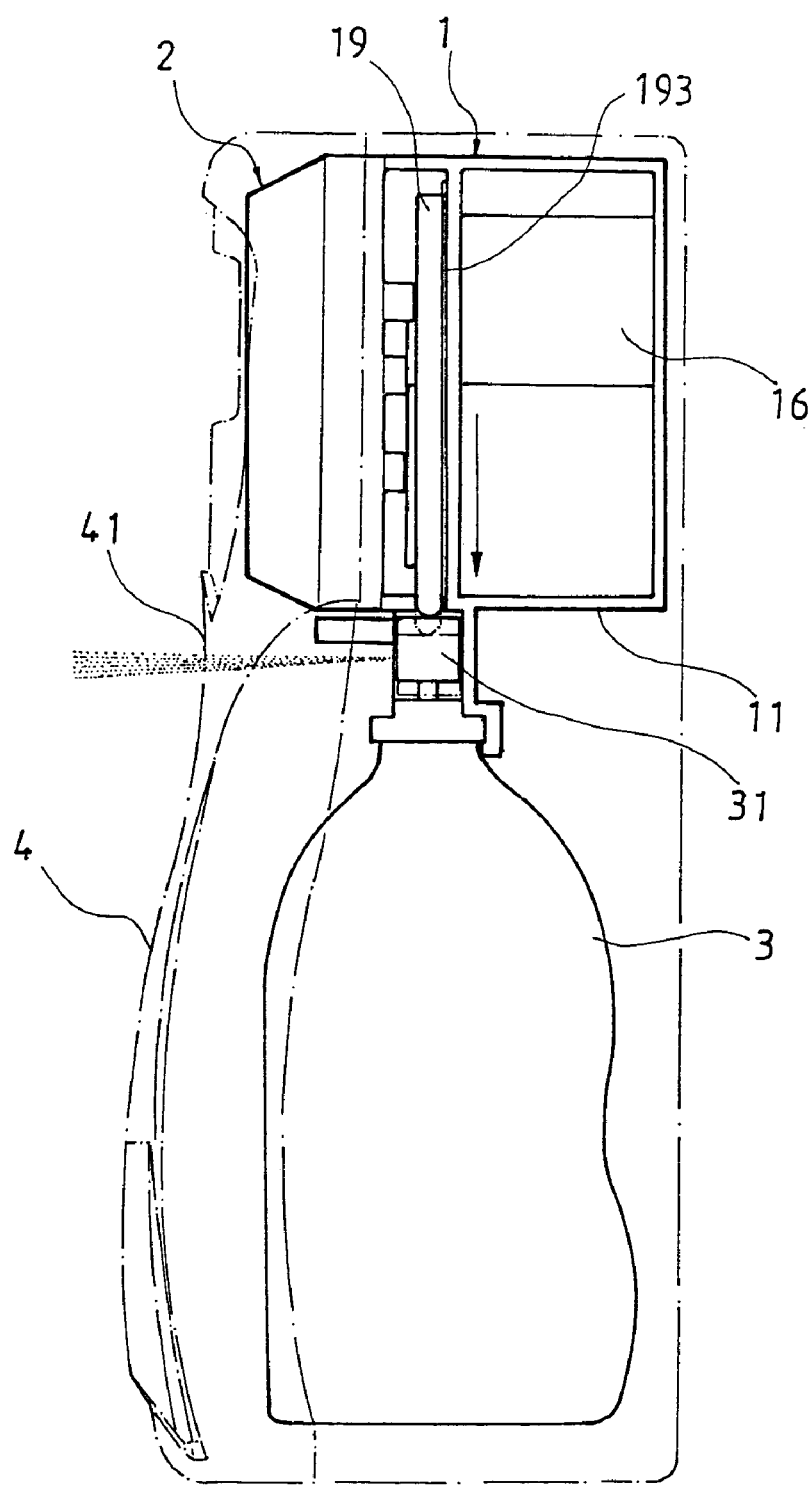

Referring to FIGS. 5 and 6, there is shown the action of the press mechanism 1. The clockwise and anticlockwise movement of the motor causes the engaged main and driven gears 17, 18 to produce movement of difference direction, wherein the press rod 19 which is in engagement with the driven gear 18 is transmitted with the gear 18 and the teeth 191, and the press rod 19 and positioning of the blocking rib 192 cause upward and downward displacement, and the position rod 31 mounted at the dispensing head of the fragrance bottle is pressed, therefore, the fragrance within the fragrance bottle 3 is dispensed via the nozzle 41 of the body 4. The recess 12 is adaptable to fragrance bottle of aqueous soluble or inert gas soluble.

Figure 7:
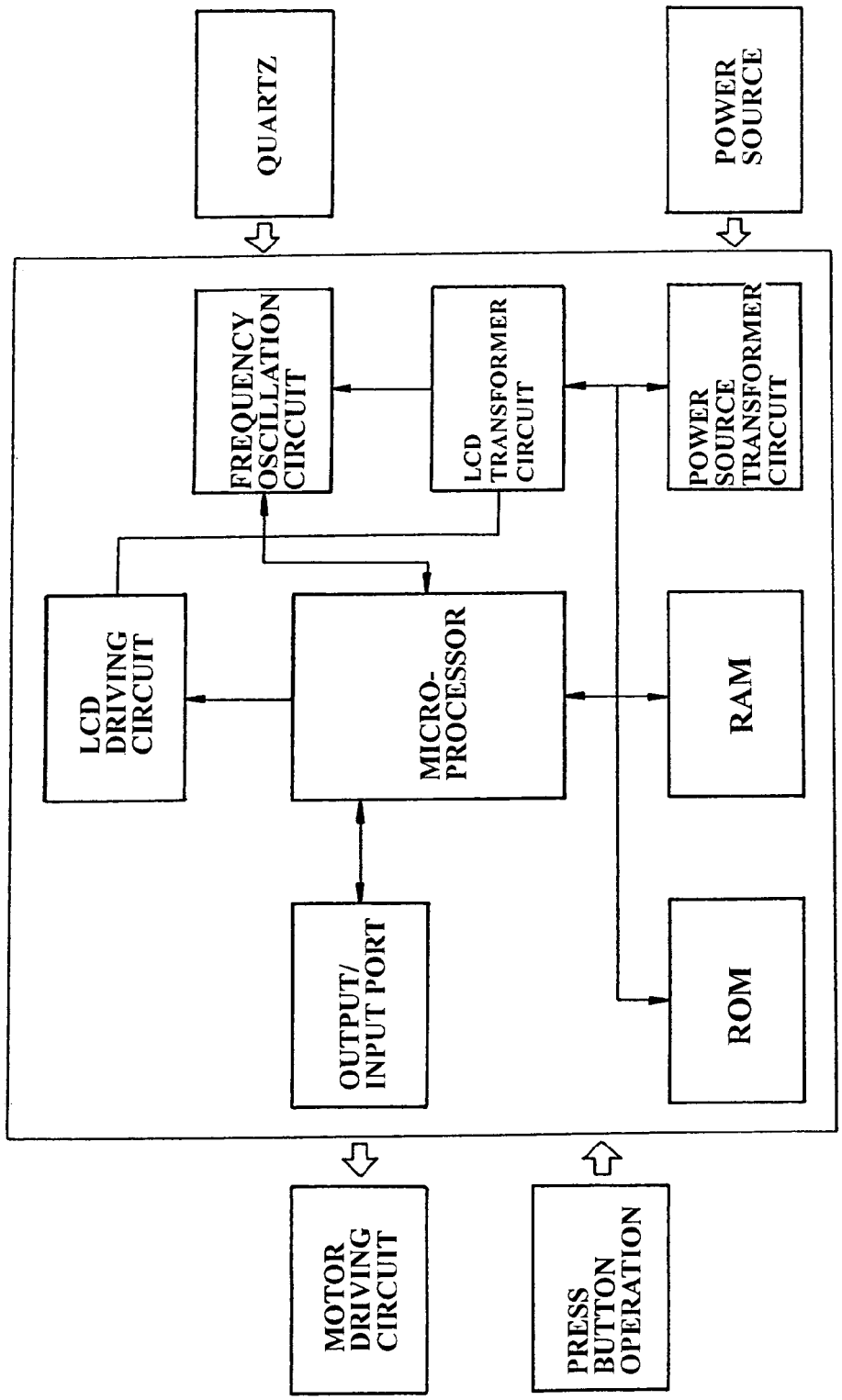
FIG. 7 is a block diagram of the control circuit in accordance with the present invention.

Referring to FIG. 7, there is shown the circuit diagram in accordance with the present invention. As shown in the figure, the control circuit 2 includes a microprocessor and memory, LCD driver, input/output port, and by means of the press button 22, the working days of the fragrance and the total numbers of dispensing of fragrance are set. The microprocessor based on the set value, will calculate the timing of dispensing and is stored within the memory and displayed on the LCD such that the fragrance dispenser will automatically dispense fragrance at the set timing. Thus, the date of changing a new bottle of fragrance can be exactly determined.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

I claim:

1. A driving mechanism for fragrance dispenser including a press mechanism and a control circuit characterized in that the press mechanism is provided with a base seat having a protruded circular recess at the lower section thereof for the mounting of a fragrance bottle, the surface of the base seat is mounted with engageable main and driven gears, and the bottom of the base seat is provided with a motor such that the axle of the motor and the main gear are engaged with each other, and the driven gear is engaged with a press rod having a plurality of teeth such that the driving by the control circuit will drive the gear to rotate and the press rod is driven to move up and down, thereby the dispensing head of the fragrance bottle is pressed and the fragrance is dispensed at a specific timing, wherein the surface of the base seat is provided with a blocking rib and a pair of symmetrical protruded ribs such that the press rod urges the blocking rib and the protruded ribs and the up and down movement of the press rod provides a positioning function.

\* \* \* \* \*